(12) United States Patent
Seddigi et al.

(10) Patent No.: US 9,101,913 B2
(45) Date of Patent: Aug. 11, 2015

(54) COMPOSITION AND METHOD OF USING A CATALYST FOR PHOTO-CATALYTIC DEGRADATION OF CONTAMINANT IN WATER

(71) Applicant: Umm Al-Qura University, Makkah (SA)

(72) Inventors: Zaki S Seddigi, Makkah (SA); Saleh A Saleh, Makkah (SA)

(73) Assignee: Umm-Al-Qura University, Makkah (SA)

( * ) Notice: Subject to any disclaimer, the term of this patent is extended or adjusted under 35 U.S.C. 154(b) by 15 days.

(21) Appl. No.: 13/950,084

(22) Filed: Jul. 24, 2013

(65) Prior Publication Data

US 2015/0031141 A1    Jan. 29, 2015

(51) Int. Cl.
*G01N 33/22* (2006.01)
*G01N 33/00* (2006.01)
*B01J 23/63* (2006.01)

(52) U.S. Cl.
CPC ...................................... *B01J 23/63* (2013.01)

(58) Field of Classification Search
CPC ..... G01N 31/22; G01N 31/229; G01N 31/00; G01N 33/52; G01N 33/50; G01N 33/00; G01N 33/22; G01K 3/04; G01K 3/00; B82Y 30/00; B01J 23/63; B01J 22/56; B01J 23/54; B01J 23/38; B01J 23/00

USPC ............................................. 436/2, 128, 127
See application file for complete search history.

(56) References Cited

U.S. PATENT DOCUMENTS 5,559,275 A * 9/1996 Barger .......................... 568/905

OTHER PUBLICATIONS

Schuyten, Stephen J., Activity and In-Situ XAS Studies of Promoted Copper and Zinc Oxide Catalysts for Hydrogen Productin by Methanol Partial Oxidation, Feb. 2008, University of Notre Dame, pp. 1-264.*
Liang, Hongying et al., Aqueoud co-precipitation of Pd-doped cerium oxide nanoparticles: chemistry, structure, and particle growth, J Mater Sci, 2012, 47, pp. 299-307.*
STN Search Report for U.S. Appl. No. 13/950,084 obtained on May 27, 2015. pp. 1-74.*

* cited by examiner

*Primary Examiner* — Christine T Mui
(74) *Attorney, Agent, or Firm* — Geeta Kadambi; Riddhi IP LLC

(57) ABSTRACT

This invention relates to the preparation and making use of a catalyst for the photo-catalytic degradation of methyl tertiary butyl ether (MTBE) in water. Palladium doped on composite Cerium oxide-zinc oxide ($Ce_2O_3$—ZnO) photo-catalyst was prepared by wetness incipient impregnation method. This catalyst composition demonstrated 99.6% degradation of MTBE at room temperature in a photo catalytic reaction conducted in oxygen saturated aqueous medium in the presence of UV light.

8 Claims, 8 Drawing Sheets

Step-wise synthesis of Pd/Ce$_2$O$_3$-ZnO photo-catalyst

SEM micrograph of 1% Pd doped Ce$_2$O$_3$-ZnO photo-catalyst

TEM image of 1% Pd/Ce$_2$O$_3$-ZnO photo-catalyst

EDX spectra of 0.5% Pd doped Ce$_2$O$_3$-ZnO photo-catalyst

EDX spectra of 1% Pd doped Ce$_2$O$_3$-ZnO photo-catalyst

XRD diffractogram of 1% Pd doped $Ce_2O_3$-ZnO photo-catalyst

Step-wise process of MTBE degradation using Pd/ Ce$_2$O$_3$-ZnO photo-catalyst

Photo-catalytic degradation of MTBE in water in presence of Pd/ $Ce_2O_3$-ZnO photo-catalyst Reaction kinetics of photo-catalytic degradation of MTBE in water in presence of Pd/ $Ce_2O_3$-ZnO photo-catalyst

COMPOSITION AND METHOD OF USING A CATALYST FOR PHOTO-CATALYTIC DEGRADATION OF CONTAMINANT IN WATER

FIELD OF TECHNOLOGY

The disclosure generally relates to a novel composition of a catalyst and a method of using the catalyst for degradation of ether-based compounds. More specifically, the present invention relates to a novel composition of a palladium doped cerium-zinc oxide photo-catalyst and its use for degradation of MTBE in contaminated water.

BACKGROUND

Fuel oxygenates were introduced in the petroleum industry in the past which helped in eliminating the use of leaded gasoline and to improve octane value of gasoline. Also, it leads to a near complete combustion of fuel by supplying much needed oxygen during the combustion process (Day et al. 2001). Fuel oxygenates are basically aliphatic alcohol based or ether based compounds. Aliphatic alcohol based fuel oxygenates require extra careful handling to avoid any water content whereas ether based fuel oxygenates are on the other hand easy to mix with gasoline without much of hassles. Therefore, ether-based fuel oxygenates such as ethyl tertiary-butyl ether (ETBE) or methyl tertiary-butyl ether (MTBE) were started to be preferably blended with gasoline (Kanai et al. 1994).

Thus, the use of MTBE became common in petro industry and hence increased its consumption ultimately leading to its reaching contamination levels in the environment. Some of the reasons for the contamination of MTBE in environment are its inflammable nature, solubility in water, non-absorbance in soil and resisting bio-degradation. Thus, it poses a high risk to human health and can get accumulated in blood stream, cause cough, dizziness, fever, headaches, muscular aches, vomiting, sleepiness and skin and eye irritation (Amir et al. 2012; Baus et al. 2005) among other problems. There is no definite method to control MTBE's entry into the environment and also to degrade the already present MTBE contamination in the environment.

SUMMARY

The present invention disclosure relates to a preparation of a novel composition of a catalyst and a process of using the catalyst for the photo-catalytic degradation of environmental contaminant in water. Further, the present invention relates to a preparation of a novel composition of a photo-catalyst and a process of using the photo-catalyst for the photo degradation of MTBE contamination in water.

In one embodiment, a novel composition of a catalyst as disclosed is a metal doped composite cerium oxide-zinc oxide ($Ce_2O_3$—ZnO) photo-catalyst. In another embodiment, metal doped in making the photo-catalyst as disclosed is a platinum group metal, preferably palladium (Pd) doped $Ce_2O_3$—ZnO photo-catalyst.

In one embodiment, a method of synthesis of $Ce_2O_3$—ZnO composite from a zinc nitrate hexahydrate and a cerium nitrate hexahydrate is disclosed. In another embodiment, a method of synthesis of $Ce_2O_3$—ZnO composite is by a co-precipitation method is disclosed. The method as disclosed comprise of mixing a zinc nitrate hexahydrate and a cerium nitrate hexahydrate to form a solution; adding an ethylene glycol to the solution; adding a sodium carbonate to the solution to form a precipitate; separating the precipitate by centrifugation to form a precursor of cerium oxide-zinc oxide ($Ce_2O_3$—ZnO) composite.

In one embodiment, the zinc nitrate hexahydrate and cerium nitrate hexahydrate are mixed to form an aqueous solution. In another embodiment, the zinc nitrate hexahydrate and cerium nitrate hexahydrate are mixed in pre-determined ratios to form an aqueous solution. In most embodiments, the zinc nitrate hexahydrate and cerium nitrate hexahydrate are mixed in equal molar ratios to form an aqueous solution.

In one embodiment, the zinc nitrate hexahydrate and cerium nitrate hexahydrate are mixed in a desired medium to form a solution.

In one embodiment, the solution of the zinc nitrate hexahydrate and cerium nitrate hexahydrate may be mixed to form a solution with continuous stifling at room temperature for a period of 2 hours. In another embodiment, the solution of the zinc nitrate hexahydrate and cerium nitrate hexahydrate may be mixed with stifling at a pre-determined temperature for a required interval of time as per the experimental setup.

In one embodiment, a required amount of sodium carbonate is added to the solution to reach a desired pH as per the experimental setup, a required amount of sodium carbonate is added to the solution to reach a pH 10.0 for the solution, in another embodiment.

The method of synthesis of the precursor of $Ce_2O_3$—ZnO composite as disclosed above further comprise of washing the precursor of cerium oxide-zinc oxide composite with de-ionized water followed by washing with an ethanol; drying the precursor cerium oxide-zinc oxide composite in air at a specific temperature; calcining the dried precursor of cerium oxide-zinc oxide composite to obtain a cerium oxide-zinc oxide particle. In one embodiment, precursor of cerium oxide-zinc oxide composite is dried in air at a temperature of 100° C. overnight, whereas it may be dried at a pre-determined temperature other than 100° C.

In one embodiment, a process of calcination of the dried precursors of cerium oxide-zinc oxide is carried at a temperature range of 400° C. to 600° C. for 4 hours to 8 hours to obtain the cerium oxide-zinc oxide particle. In most embodiments, the process of calcination of the dries precursors of cerium oxide-zinc oxide precursors is carried at 450° C. for 6 hours to obtain the cerium oxide-zinc oxide particle.

In one embodiment, a metal is doped onto synthesized $Ce_2O_3$—ZnO particle to obtain metal doped catalyst. In another embodiment, Pd is doped onto synthesized $Ce_2O_3$—ZnO particles to obtain Pd/$Ce_2O_3$—ZnO photo-catalyst. Thus, further, aspect of the invention discloses a method of doping Pd onto synthesized $Ce_2O_3$—ZnO particle by wetness incipient impregnation method. The method of doping Pd onto synthesized $Ce_2O_3$—ZnO particle as disclosed comprise of dissolving a pre-determined amount of a palladium (II) nitrate dihydrate ($Pd(NO_3)_2.2H_2O$) in a deionized water to form a Pd nitrate impregnated $Ce_2O_3$—ZnO particle; drying the Pd impregnated $Ce_2O_3$—ZnO particle; exposing the Pd impregnated $Ce_2O_3$—ZnO particles to ammonia vapors for a required time; mixing and drying the Pd impregnated $Ce_2O_3$—ZnO particle and calcining the Pd impregnated $Ce_2O_3$—ZnO particle to obtain a Pd/$Ce_2O_3$—ZnO photo-catalyst.

In one embodiment, the precursor of cerium oxide-zinc oxide composite is further used to synthesize Palladium/cerium oxide-zinc oxide photo-catalyst.

Adding cerium oxide onto the ZnO is expected to provide additional oxygen required for photochemical reaction and therefore will contribute to the stability of the catalyst and the said catalyst can be recycled several times adding to the cost effectiveness of the novel catalyst disclosed in this application.

In one embodiment, the Pd nitrate impregnated $Ce_2O_3$—ZnO are dried at a heating rate of 0.1 to 1.0° C./min from room temperature to 100° C. In another embodiment, Pd nitrate impregnated $Ce_2O_3$—ZnO is dried at a heating rate of 0.33° C./min from room temperature to 85° C. Further, Pd impregnated particles are exposed to ammonia vapors for a time period of 5-20 minutes preferably 10 minutes and dried overnight in air at 100° C. Pd impregnated particles are exposed to ammonia to avoid melting of Pd nitrate before decomposition thus resulting in high dispersion of Pd particles on $Ce_2O_3$—ZnO.

In one embodiment, a process of calcining the Pd impregnated particles to obtain Pd/$Ce_2O_3$—ZnO catalyst is performed at a temperature range of 400° C. to 600° C. and between 0 hrs to 8 hrs at a heating rate of 1-2° C. /min. In a preferred embodiment, a process of calcining the Pd impregnated $Ce_2O_3$—ZnO particles to a obtain Pd/$Ce_2O_3$—ZnO catalyst is performed at a temperature of 450° C. for 6 hrs at a heating rate of 1° C./min.

In one embodiment, palladium (II) nitrate dihydrate (Pd$(NO_3)_2.2H_2O$) in the weight ranging from 0.5% to 1.5% is used for doping onto $Ce_2O_3$—ZnO particles. In another embodiment, 0.5% by weight palladium (II) nitrate dihydrate (Pd$(NO_3)_2.2H_2O$) is doped onto $Ce_2O_3$—ZnO particles. In preferred embodiment, palladium (II) nitrate dihydrate (Pd$(NO_3)_2.2H_2O$) 1.0% by weight is doped onto $Ce_2O_3$—ZnO particles. In most embodiments, palladium(II) nitrate dihydrate (Pd$(NO_3)_2.2H_2O$) 1.5% by weight is doped onto $Ce_2O_3$—ZnO particles. In the present disclosure, a method of using Pd/$Ce_2O_3$—ZnO catalyst as a photo-catalyst.

In one embodiment, a method of using Pd/$Ce_2O_3$—ZnO catalyst for photo-catalytic degradation of impurities is disclosed. In another embodiment, the method of using Pd/$Ce_2O_3$—ZnO catalyst for photo-catalytic degradation of MTBE in water is disclosed.

In one embodiment, a pre-determined amount of metal doped $Ce_2O_3$—ZnO catalyst is added into deionized water. In another embodiment, a pre-determined amount of metal doped $Ce_2O_3$—ZnO catalyst is added into deionized water containing MTBE and is loaded onto a photochemical reactor. In one embodiment, the photochemical reactor has two side arm fitted with a cooling jacket. In another embodiment, the photochemical reactor has two side arm quartz fitted with a cooling jacket. The cooling jacket as stated has a cooling water system running throughout the photo-degradation process or for prescribed duration depending on the experimental setup. Further, the temperature of water running in the cooling jacket is set between 10° C. to 40° C. preferably 25° C. using a thermostatic water circulating bath or other desired means of reaching and maintaining a pre-determined temperature.

In one embodiment, a high pressure mercury lamp fitted with a tube is inserted into a reaction solution. In another embodiment, a 125 wt. UV high pressure mercury lamp fitted with long Teflon tube is inserted into the reaction solution.

In one embodiment, a process of photo-degradation by the synthesized photo-catalyst is disclosed comprising of fitting a cooling jacket to a photochemical reactor; adding distilled water, a synthesized catalyst and a contaminant to form a solution; stifling the solution at room temperature without any exposure to UV light; collecting a sample to determine the initial concentration of a contaminant (C.); saturating the solution by passing an inert gas at a pre-determined rate for a specific time period and re-collecting the sample; removing the oxygen inlet tube and switching ON the UV light followed by collecting the sample at pre-determined time intervals to assess the rate of photo-degradation of contamination.

In another embodiment, a process of photo-degradation of MTBE by Pd/$Ce_2O_3$—ZnO photo-catalyst is disclosed comprising of fitting a cooling jacket; adding a Pd/$Ce_2O_3$—ZnO photo-catalyst into a deionized water containing MTBE and forming a solution; loading the solution onto a photochemical reactor and stifling continuously; collecting a sample from de-ionized water containing MTBE and designating as an initial concentration of MTBE (C.); saturating the sample by passing an oxygen; collecting the next sample from de-ionized water containing MTBE; exposing the sample to a UV light; collecting the sample at regular intervals of time and estimating the amount of MTBE in collected samples using a gas chromatography.

In one embodiment, an inert gas is bubbled into the solution at an appropriate rate and time to saturate the solution. In preferred embodiment, an oxygen is bubbled into the solution at an appropriate rate and time to saturate the solution. Oxygen is bubbled into the photochemical reactor at a rate of about 50 cc/minute for a period of 30 minutes with continuous stifling. Further, as disclosed above a saturated sample with contaminant such as MTBE is exposed to UV light for a specific time period.

In one embodiment, oxygen inlet tube is removed before UV lamp is powered ON whereas in another embodiment, oxygen inlet tube is removed after UV lamp is powered ON.

In one embodiment, the UV lamp is fitted with long-teflon tube inserted into the solution in photochemical reactor. In another embodiment, the UV lamp is high pressure mercury lamp. The UV lamp is powered ON for a specific period of time in the photochemical reactor. In one embodiment, the catalyst is added before UV lamp is powered ON whereas in another embodiment, the catalyst is added after the UV lamp is powered ON and the solution is exposed for a required period of time.

In one embodiment, the samples are collected at regular intervals of time and samples are characterized by the gas chromatography equipped with a flame ionization detector. In another embodiment, the sample is characterized using known methods in the art.

The novel composition of a photo-catalyst and a method of using the catalyst for degradation of MTBE in water, disclosed herein, may be implemented in any means for achieving various aspects. Other features will be apparent from the accompanying Fig. and from the detailed description that follows.

BRIEF DESCRIPTION OF THE DRAWINGS

Example embodiments are illustrated by way of example and no limitation in the graph and in the accompanying Fig., like references indicate similar elements and in which.

Other features of the present embodiments will be apparent from the accompanying detailed description that follows.

DETAILED DESCRIPTION

The present disclosure relates to a novel composition of a photo-catalyst, method of making the photo-catalyst and using the photo-catalyst for the photo-catalytic degradation of MTBE in water.

Heterogeneous photo-catalysis, a member of advanced oxidation processes (AOP), has been widely applied for the treatment of toxic and non-biodegradable compounds from the environment. Photo-catalysis is simple and very promising technique for solving various environmental and energy issues. Environmental pollution and problems associated with the presence and ever increasing mass/volume of organic, toxic and non-biodegradable pollutants etc. provide the impetus for fundamental and applied research to solve these issues [Chan et al. 2003]. Typically, photo-catalysis is initiated by the irradiation of photo-catalyst, mainly semiconducting metal oxides, with light of sufficient energy to excite electron from valence band of photo-catalyst to conduction band. When electron leaves its valence band to conduction band it creates a hole in the valence band, therefore, electron-hole pair is generated as a result of photo-excitation and reacts with hydroxyl ions/oxygen/water to produce hydroxyl (.OH) radicals. These hydroxyl (.OH) radicals react with the organic molecules adsorbed on the photo-catalyst and degrade them to $CO_2$ and $H_2O$ through a series of possible chemical reactions.

Synthesis of a Photo-catalyst as Disclosed

Cerium nitrate hexahydrate, zinc nitrate hexahydrate, methyl tert-butyl ether (MTBE) from Sigma-Aldrich of 99.9% purity, palladium (II) nitrate dihydrate from Merck and double distilled water were used in this work.

Preparation of $Ce_2O_3$—ZnO particles: There are a number of commercial and non-commercial/laboratory procedures available for the preparation of $Ce_2O_3$—ZnO particles and a person skilled in the art can use any one of the processes for the preparation of $Ce_2O_3$—ZnO particles.

Figure 1:
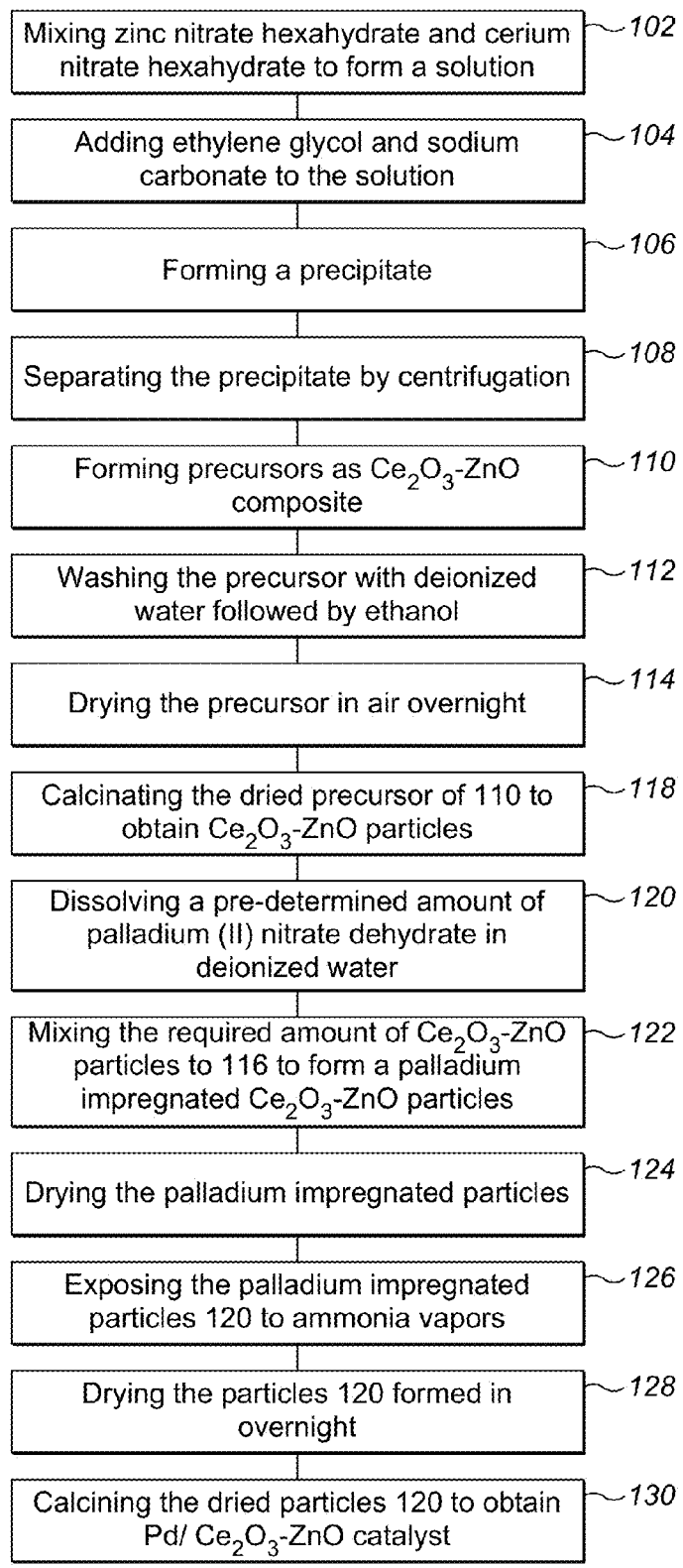
FIG. 1 shows a flow chart for the synthesis of Pd/$Ce_2O_3$—ZnO photo-catalyst.

Cerium oxide zinc oxide ($Ce_2O_3$—ZnO) particle in the present application was prepared by a co-precipitation method. As shown in FIG. 1, the steps of co-precipitation method comprise of mixing aqueous solution of required molar ratios of a zinc nitrate hexahydrate and a cerium nitrate hexahydrate with continuous stifling at room temperature for 2 hours 102; adding a small amount of ethylene glycol 104 as a structure modifying agent to the formed solution; adding appropriate amount of sodium carbonate 104 to the solution to make the pH 10.0 of the solution; forming a precipitate 106 and separating the precipitate by centrifugation 108 leading to the formation of precursor as $Ce_2O_3$—ZnO composite 110; washing the prepared precursor of Cerium oxide-zinc oxide composite thoroughly with de-ionized water followed by washing with ethanol 112; drying the prepared precursor of cerium oxide-zinc oxide composite in air at 100° C. overnight 114 and calcining the dried precursor of cerium oxide-zinc oxide composite 116 at 500° C. for 6 hours to obtain $Ce_2O_3$—ZnO particles 116.

The addition of cerium (Ce) into the matrix of ZnO is expected to provide additional oxygen required for photo-chemical reaction and therefore will contribute to the stability of the catalyst and the said catalyst can be recycled several times adding to the cost effectiveness of the novel catalyst disclosed in this application. As disclosed in the present application, a dramatic improvement in the catalyst efficiency is achieved by doping small amount of palladium on the surface of $Ce_2O_3$—ZnO particles. Palladium as palladium (II) nitrate dihydrate ($Pd(NO_3)_2.2H_2O$) in the range of 0.5% to 1.5% by weight may be loaded onto the cerium oxide-zinc oxide particle.

Synthesis of Pd/$Ce_2O_3$—ZnO catalyst: Pd/$Ce_2O_3$—ZnO photo-catalyst as disclosed in the present application is synthesized by using wetness incipient impregnation method. The method as disclosed, comprise of mixing a pre-determined amount of palladium(II) nitrate dihydrate ($Pd(NO_3)_2.2H_2O$) in deionized water 118 to form enough solution to cover cerium oxide-zinc oxide particle; mixing required amount of a cerium oxide-zinc oxide particle to palladium(II) nitrate dihydrate ($Pd(NO_3)_2.2H_2O$) solution formed above 118 to form a Pd impregnated cerium oxide-zinc oxide particle 120; drying the Pd impregnated cerium oxide-zinc oxide particle by heating the solution at a rate of 0.33° C./min from room temperature up to 85° C. 122; exposing the Pd impregnated cerium oxide-zinc oxide particle to an ammonia vapor for 10 minutes 124. This step is performed to avoid melting of Pd nitrate before decomposition thus resulting in high dispersion of a nano Pd particle on Pd/$Ce_2O_3$—ZnO photo-catalyst. The synthesis further comprise of drying the Pd impregnated cerium oxide-zinc oxide particle from 124 overnight in air at a temperature of 100° C. 126. The dried Pd impregnated cerium oxide-zinc oxide particle from 126 was calcined at 450° C. for 6 hours at a heating rate of 1° C./min to obtain a Pd/$Ce_2O_3$—ZnO photo-catalyst 128.

Pd is doped on the synthesized $Ce_2O_3$—ZnO composite using wetness incipient impregnation method as disclosed. Pd in the w % range of 0.5%-1.5% may be doped onto synthesized $Ce_2O_3$—ZnO composite to form a 0.5% Pd/$Ce_2O_3$—ZnO photo-catalyst, a 1.0% Pd/$Ce_2O_3$—ZnO photo-catalyst and a 1.5% Pd/$Ce_2O_3$—ZnO photo-catalyst respectively and is further used for a photocatalytic degradation of MTBE in water. Pd loading onto $CeO_2$ has been reported to change the surface properties of the support material, which results from the electron-transfers between Ce and palladium [Faisal et al. 2011]. Also, Pd doping on Ce as support or promoter are very important due to the unique acid-base and redox properties of Ce which further influences: the redox reactions of supported noble metals, the catalytic property of metal crystallites, the thermal resistance supporting material and dispersion of supported metals etc. [Xiaohong et al. 2006]

Characterization of Photo-catalyst

The synthesized photo-catalyst as disclosed in the present application was further characterized using advance instrumentation techniques such as scanning electron microscopy (SEM), transmission electron microscopy (TEM), EDX analysis and x-ray diffraction (XRD) pattern studies.

Figure 2:
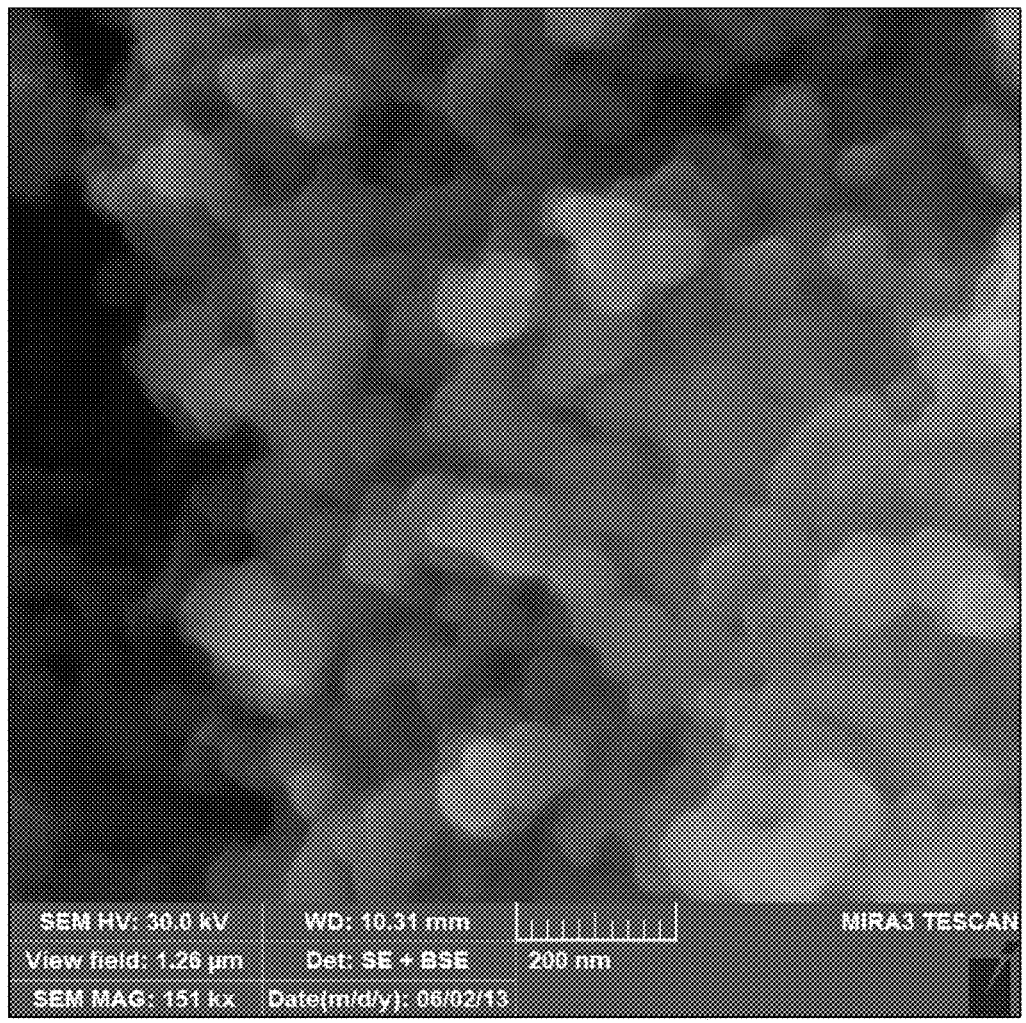
FIG. 2 shows a SEM micrograph of 1% Pd doped $Ce_2O_3$—ZnO photo-catalyst.
Figure 3:
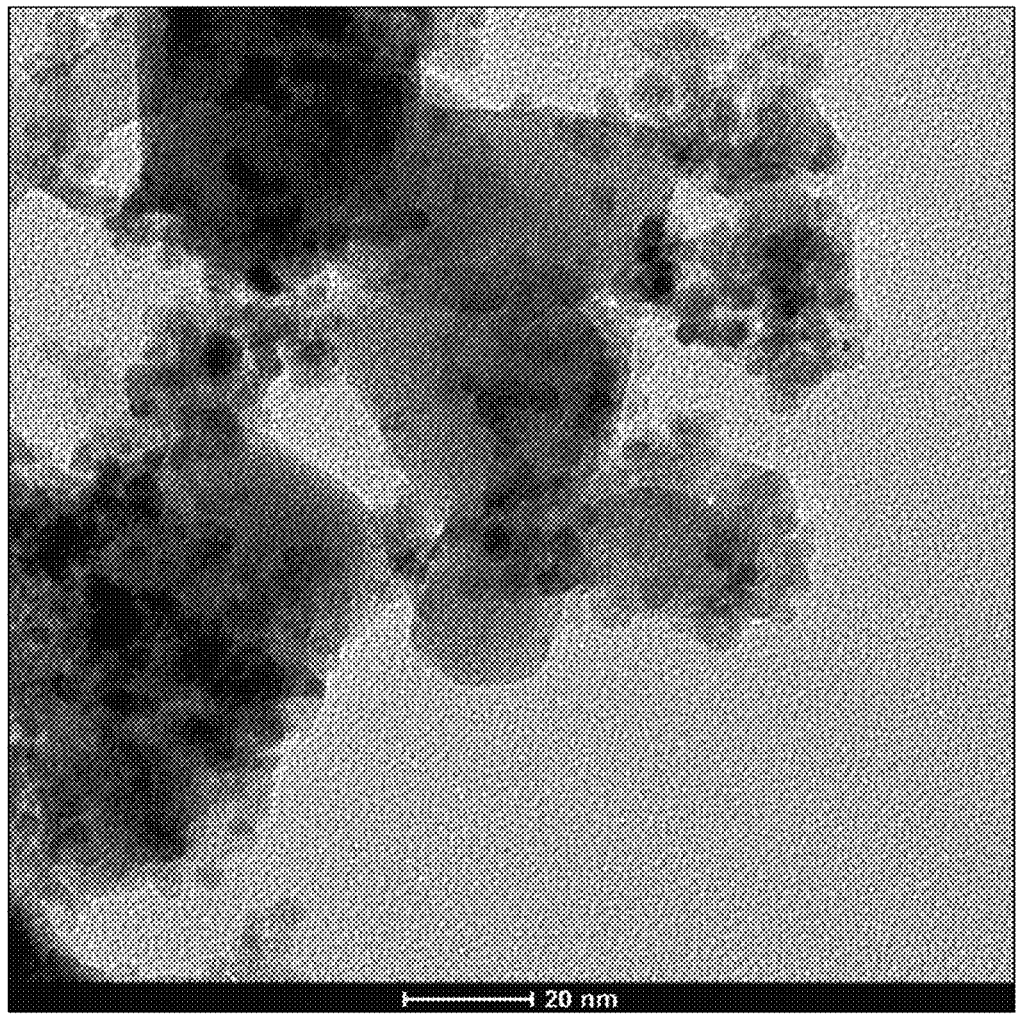
FIG. 3 shows a TEM image of 1% Pd/$Ce_2O_3$—ZnO photo-catalyst.
Figure 5:
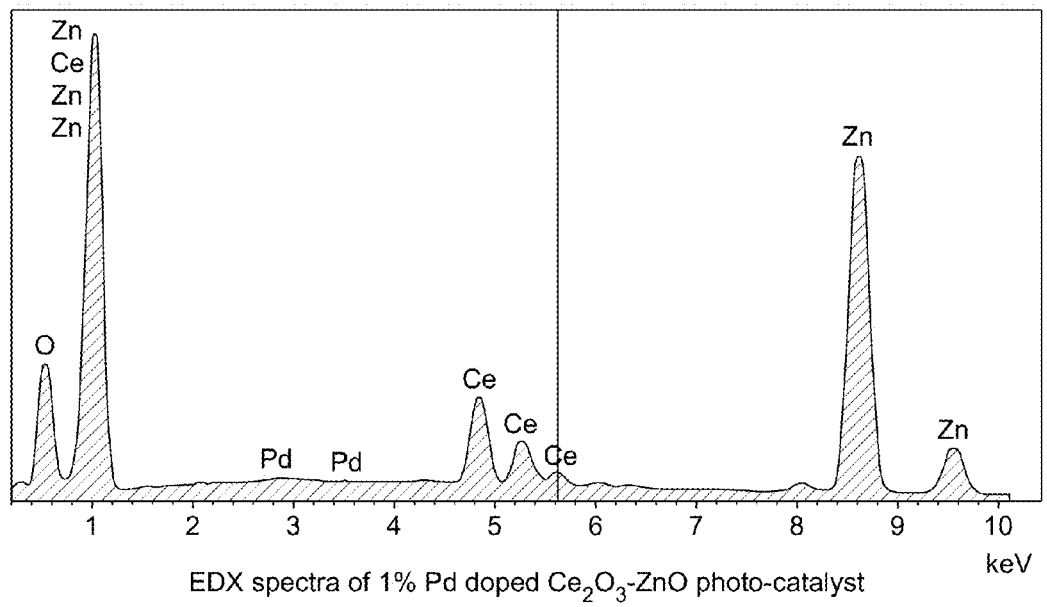
FIG. 5 shows an EDX spectra of 0.5% Pd doped $Ce_2O_3$—ZnO photo-catalyst.
Figure 6:
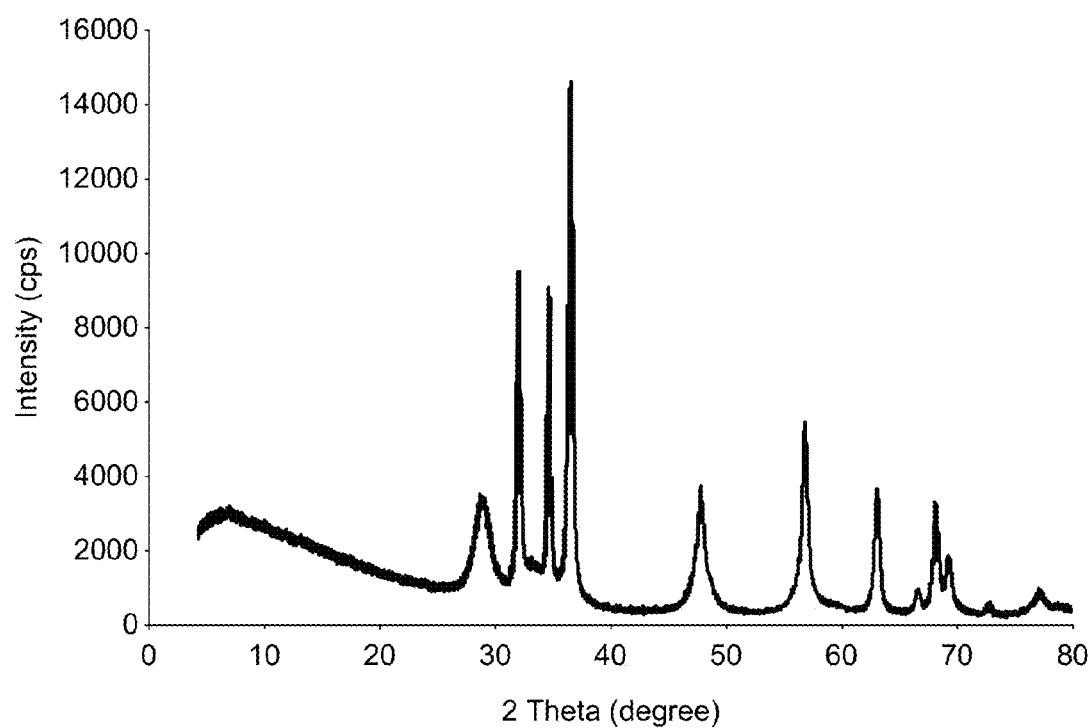
FIG. 6 shows a XRD diffractogram of 1% Pd doped $Ce_2O_3$—ZnO.

As shown in FIG. 2, the morphology of disclosed and synthesized photo-catalyst (1% Pd—$Ce_2O_3$—ZnO) is observed by SEM and show that they are round in shape with uniform size distribution. As observed, the particles size of the Pd—$Ce_2O_3$—ZnO photo-catalyst such as the 1% Pd—$Ce_2O_3$—ZnO photo-catalyst lies in the range of 6-33 nm. The results were further confirmed by TEM images as shown in FIG. 3. Two types of particles are clearly shown in composite $Ce_2O_3$—ZnO photo-catalyst. Further, EDX analysis of 0.5% Pd—Ce$_2$O$_3$—ZnO photo-catalyst (FIGS. 4) and 1.0% Pd—Ce$_2$O$_3$—ZnO photo-catalyst (FIG. 5) shows the presence of all the components including Pd with the Ce and Zn. Further, the 1% Pd—Ce$_2$O$_3$—ZnO photo-catalyst sample was also analyzed by XRD diffractometer (FIG. 6). The crystalline structure of the 1% Pd/Ce$_2$O$_3$—ZnO photo-catalyst was characterized by a rotating-target X-ray diffractometer (Japan Rigaku D/Max-2400) equipped with a monochromatic high-intensity Cu K radiation (=1.5418 Å, 40 kV, 100 mA). The average crystalline size of the photo-catalyst was estimated from the full width half maximum (FWHM) and the peak position of an XRD line broadened according the Scherrer formula [Hayat et al. 2011]:

$$d = [0.9\lambda/B \cos \theta] \quad \text{(Equation 1)}$$

where 'd' is the average crystallite size, λ is the wavelength of the X-ray (0.15418 nm), B is the full width at half maximum (FWHM, radian) and θ is the Bragg angle (degree). The value of FWHM was obtained by performing profile fitting using an XRD pattern processing software. The characteristic strong diffraction peaks obtained for the 1% Pd—Ce$_2$O$_3$—ZnO photo-catalyst are given in FIG. 6. The characteristic peaks of the individual oxide phase show that ceria particles are of much smaller in size (about 6 nm) as compared with ZnO particles (20+nm).

Photo-degradation of MTBE in Water

Figure 7:
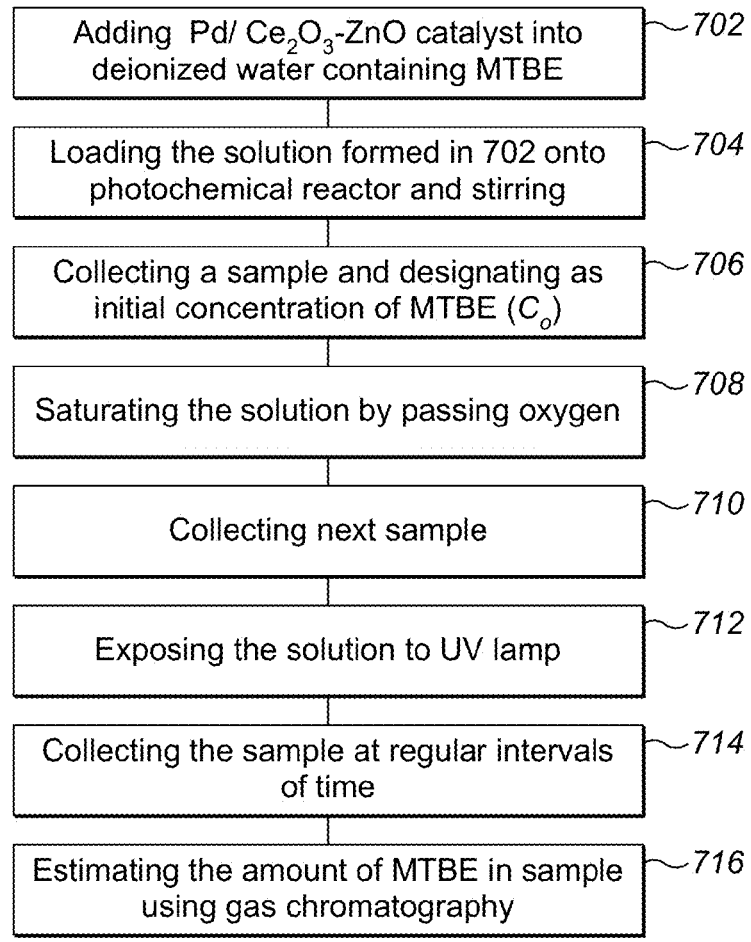
FIG. 7 shows a flow chart for method of using Pd/$Ce_2O_3$—ZnO catalyst for photo-degradation of MTBE in water.

FIG. 7 shows a step-wise photo-degradation of the MTBE by using the Pd/Ce$_2$O$_3$—ZnO photo-catalyst as synthesized above. To carry out photo-degradation, a required amount of Pd/Ce$_2$O$_3$—ZnO photo-catalyst was added into deionized water containing MTBE contamination 702 to form a solution. The solution thus formed was loaded onto a photochemical reactor 704. The solution was stirred thoroughly to disperse the Pd/nano ZnO photo-catalyst in the solution 704. Following this, a liquid sample was collected and designated as initial concentration of MTBE (C$_0$) 706. After collecting the sample, remaining solution was saturated by passing oxygen through the inlet tube into the solution 708. Again the sample was collected 710. The oxygen inlet tube was taken out of the photochemical reactor and UV lamp was powered ON for a particular time period 712. The sample was again collected at regular interval of time 714 and the amount of MTBE was calculated using a gas chromatography equipped with a flame ionization detector 716 (FIG. 7).

The photochemical reactor being used for the photo-degradation process is a double sided arms quartz photochemical reactor. The reactor is further fitted with a cooling jacket which runs cooling water throughout an experiment or for a prescribed time depending on the experimental conditions. The temperature of the cooling water system is set at 25° C. using a thermostatic water circulating bath. The temperature of the cooling water system may be set 10° C. above or 10° C. below 25° C. depending on the experimental conditions.

The photochemical reactor further comprises of a UV lamp, preferably a mercury lamp. A 125 wt. UV high pressure mercury lamp is fitted along with a long teflon tube. The assembly of the mercury lamp and the teflon tube is inserted into the reaction solution. The photochemical reactor further comprises of an oxygen inlet tube. The tube provides the necessary oxygen to saturate the reaction solution.

Further, a photo-degradation process using the disclosed photo-catalyst may also be carried out as follows: In a 500 ml two side arms photochemical reactor fitted with a cooling jacket, 500 ml of distilled water, 150 mg of the selected photo-catalyst and 100 ppm by weight of MTBE were stirred at room temperature without any radiation for a period of 30 min to have a complete dispersion of the photo-catalyst in the solution and a liquid sample was collected to be designated as initial concentration of MTBE (C$_0$). Then, a current of oxygen gas with a rate of 50 cc/min was passed through the solution via inlet tube for 30 min and a sample was collected. The oxygen inlet tube was then removed and the UV lamp was switched-ON and a system was covered with aluminum foil. Sample was collected every 1 h after starting the UV lamp for total photo-degradation period of 5 hours.

EXAMPLES

The present embodiments are being described with reference to specific example embodiments and are included to illustrate but not limit the scope of the invention.

Example 1

In the present experiment, no photo-catalyst was used to investigate the effect of only UV light on the degradation of MTBE in water. A solution of 100 ppm by weight of MTBE was placed in a photo-reactor. The solution was saturated with bubbling oxygen at a rate of 50 cc/min for a period of 30 min with continuous stirring. After that, UV lamp was powered ON and first sample was taken after 1 hour of exposure to UV light. The experiment was continued for 5 hours and sample was withdrawn after every hour. Following which the concentration of MTBE in the sample was measured with a gas chromatograph equipped with a flame ionization detector (FID).

Figure 8:
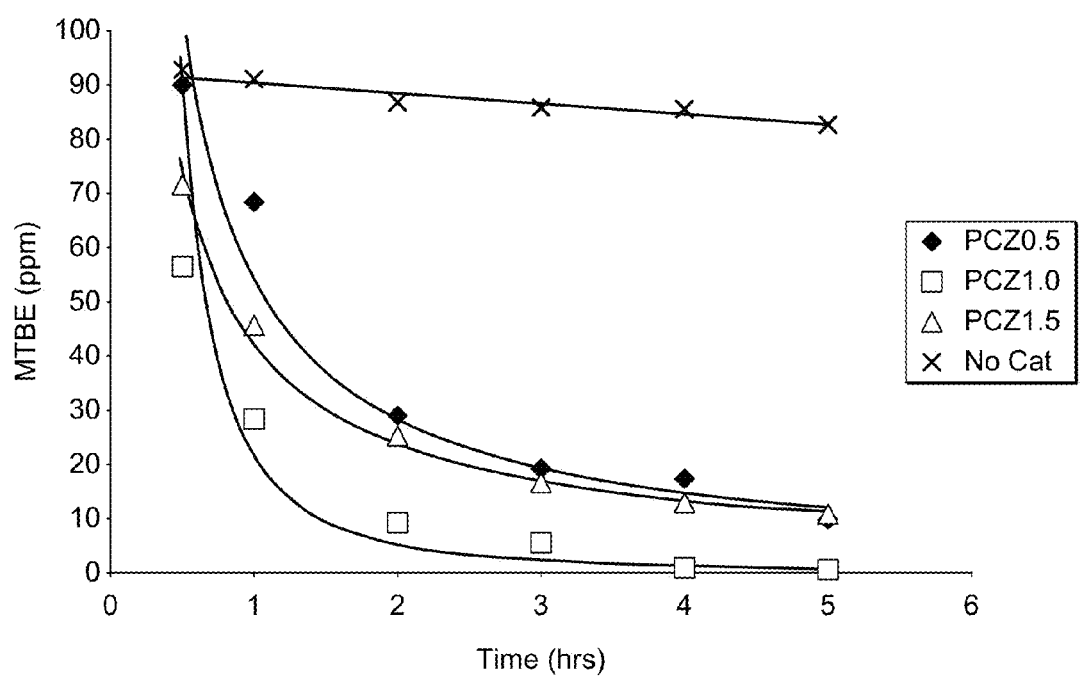
FIG. 8 shows photo-catalytic degradation of MTBE in water in presence of Pd doped $Ce_2O_3$—ZnO catalyst.

The results are plotted in FIG. 8. The results show almost negligible degradation of MTBE during 5 hours of UV exposure.

Example 2

Figure 4:
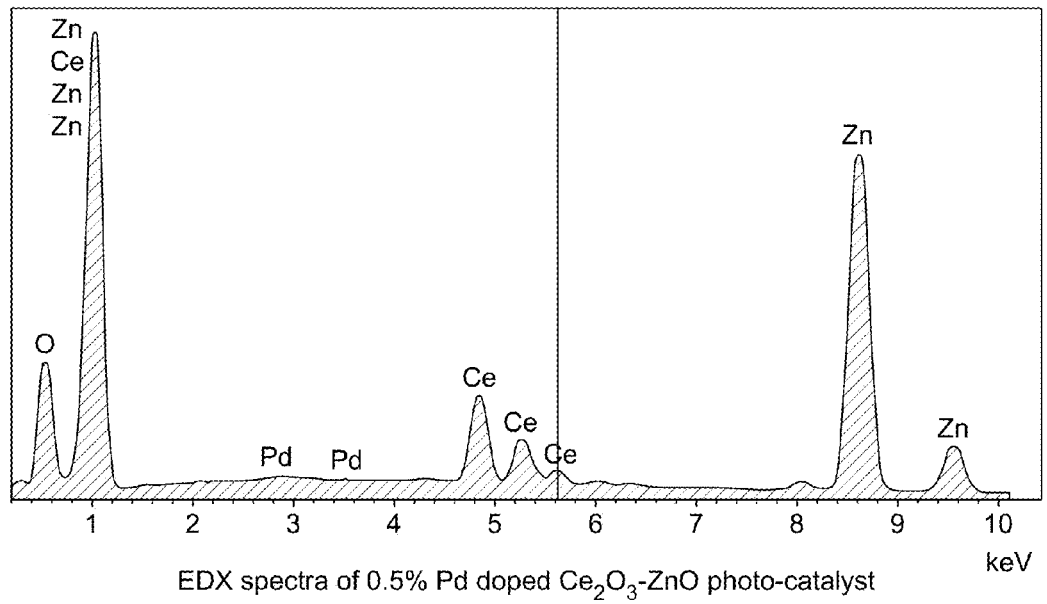
FIG. 4 shows an EDX spectra of 0.5% Pd doped $Ce_2O_3$—ZnO photo-catalyst.

Catalyst A (PCZ0.5) was prepared by doping 0.5 wt % of Pd on the synthesized cerium oxide-zinc oxide composite using wetness incipient impregnation method as disclosed above. Energy dispersive spectroscopy (EDS) was used to determine the elemental composition of the prepared catalyst samples and the corresponding results of a typical sample with 0.5 wt % Pd/Ce$_2$O$_3$—ZnO photo-catalyst is shown in FIG. 4. The results clearly indicate that Pd even at small level such as 0.5 wt % can be detected by this technique.

For the studies, 150 mg of the Catalyst A (PCZ0.5) was used in a 500 ml solution of 100 ppm by weight of MTBE in deionized water in a photo-reactor. The photo-catalytic experiment was conducted following the same procedure as described in the above example and the results are shown in FIG. 8.

Example 3

Catalyst B (PCZ1.0) was prepared following the same procedure as adopted for making of Catalyst A (PCZ0.5) with 1.0% Pd loaded on cerium oxide-zinc oxide composite. A 150 mg of the Catalyst B was used in a 500 ml solution of 100 ppm by weight of MTBE in deionized water in a photo-reactor. The photo-catalytic experiment was conducted following the same procedure as described in example 1.

The results are shown in FIG. 8. The results show near complete removal MTBE from the water in 5 hours of UV exposure in the presence of 1.0% Pd/Ce$_2$O$_3$—ZnO photo-catalyst. The final result after 5 hours of UV exposure showed 0.4 ppm MTBE on gas chromatograph that has minimum detection limit of less than 0.04 ppm.

Example 4

Catalyst C (PCZ1.5) was prepared following the same procedure as adopted for making Catalyst A (PCZ0.5) with 1.5% Pd loaded onto cerium oxide-zinc oxide composite. A 150 mg of the Catalyst C was used in a 500 ml solution of 100 ppm by weight of MTBE in deionized water in a photo-reactor. The photo-catalytic experiment was conducted following the same procedure as described in the above example 1.

The results are shown in FIG. 8. The results show 11.1 ppm of MTBE after 5 hours of exposure in the presence of 1.5% Pd/Ce$_2$O$_3$—ZnO photo-catalyst.

Thus, the results as from the studies above show that 1% Pd/Ce$_2$O$_3$—ZnO photo-catalyst has the highest photo-catalytic activity as compared to the other photo-catalyst such as 0.5% Pd/Ce$_2$O$_3$—ZnO photo-catalyst and 1.5% Pd/Ce$_2$O$_3$—ZnO photo-catalyst. Nearly complete degradation of MTBE (99.6%) was observed with 1% Pd/Ce$_2$O$_3$—ZnO photo-catalyst after 5 hours compared to the other two catalysts 0.5% Pd/Ce$_2$O$_3$—ZnO photo-catalyst (90%) and 1.5% Pd/Ce$_2$O$_3$—ZnO photo-catalyst (88.9). Therefore, 1% Pd/Ce$_2$O$_3$—ZnO photo-catalyst may be considered as an effective photo-catalyst in the degradation of MTBE in water with optimum loading of Pd. Initially, the rate of the photo-degradation of MTBE is found to be very fast as can be seen from FIG. 8. After the first hour of UV exposure, the concentration of MTBE in the reaction medium was found to be 28.2 ppm in case of cerium oxide-zinc oxide composite doped with 1% Pd. The fast photo-degradation of MTBE in the early hour can be attributed to the presence of the hydroxyl radicals (OH) whose concentration increases with the UV exposure and catalyst surface area for adsorption of MTBE. However, as the reaction proceeds, photo-catalytic degradation of MTBE decreases due to the competition offered by presence of other species in the reaction medium for the hydroxyl radical and adsorption surface. The increased efficiency of the cerium oxide-zinc oxide composite doped with 1% Pd is due to the fast transfer of the photo-excited electrons from the surface of the semiconducting photo-catalyst to the noble metal which will act as an electron reservoir [Xiaohong et al. 2006; Chan et al. 2009; Trovarelli A. 1996]. Consequently, the recombination of the photo-generated electrons and holes will be efficiently controlled which in turn increase the photo-catalytic activity of the photo-catalyst [Jakob and Levanon 2003; Neppolian et al. 2012].

The increase in photo-activity further may also be associated with a larger surface area of photo-catalyst particles and metallic dopants due to smaller sizes of the particles of both the photo-catalyst and the metallic dopant the larger will be the surface area [Orlov et al. 2007]. The presence of noble metal, i.e., palladium on the surface of the semiconducting metal oxide photo-catalyst lowers the work function at the interface with the adsorbed oxygen and thus the electron transfer between the photo-catalyst and the adsorbed oxygen will increases. This would in turn increase the number of peroxy/superoxy species which are highly oxidizing in nature and thus, increase the rate of the photo-catalytic reaction [Haruta M. 1997; Yaqin Fu and Sykes Ni 2011; Sykes et al. 2002; Hoffmann et al. 2005]. However, the concentration of the doped metallic particles was also reported to affect the activity of the photo-catalyst. On doping cerium oxide-zinc oxide composite with 1.5% Pd, the activity of the photo-catalyst was decreased. This is due to the fact that an increase in the number of the particles of the doped metal on the surface of the cerium oxide-zinc oxide composite results in fewer amounts of adsorbed MTBE and less surface open for radiation to start photo-excitation. Consequently, the photo-catalytic activity of the photo-catalyst has decreased.

The heterogeneous photo-catalysis begins with the adsorption of the organic contaminant molecules on the surface of the photo-catalyst. These adsorbed contaminant molecules will react with the hydroxyl radicals produced as a result of reaction between water and the photo-generated electrons/holes which in turn are generated as a result of photo-excitation process. The heterogeneous photo-catalytic degradation of the various pollutants in water has been found to follow Langmuir-Hinshelwood kinetic model [Hayat et al. 2011]. Accordingly, the rate of the photo-catalytic degradation of the organic pollutants is proportional to the surface area coverage of the photo-catalyst by the organic pollutant molecules:

$$\text{Rate } (R) = -(dC/dT) \, \alpha \theta \quad \text{(Equation 2)}$$

$$= k_r \theta = (k_r KC/1 + KC), \quad \text{(Equation 3)}$$

If $KC \ll 1$ and negligible $$-\ln(C/C_0) = K_{app} t \quad \text{(Equation 4)}$$

Where θ, $k_r$, K, C defines the surface area covered, rate constant of the photo-catalytic degradation reaction, the adsorption coefficient of the reactant and the reactant concentration respectively. If the concentration C becomes very low, KC would be negligible compared to 1. A plot of ln (C$_0$/C) versus irradiation time gives a straight line which represents a first order reaction.

Figure 9:
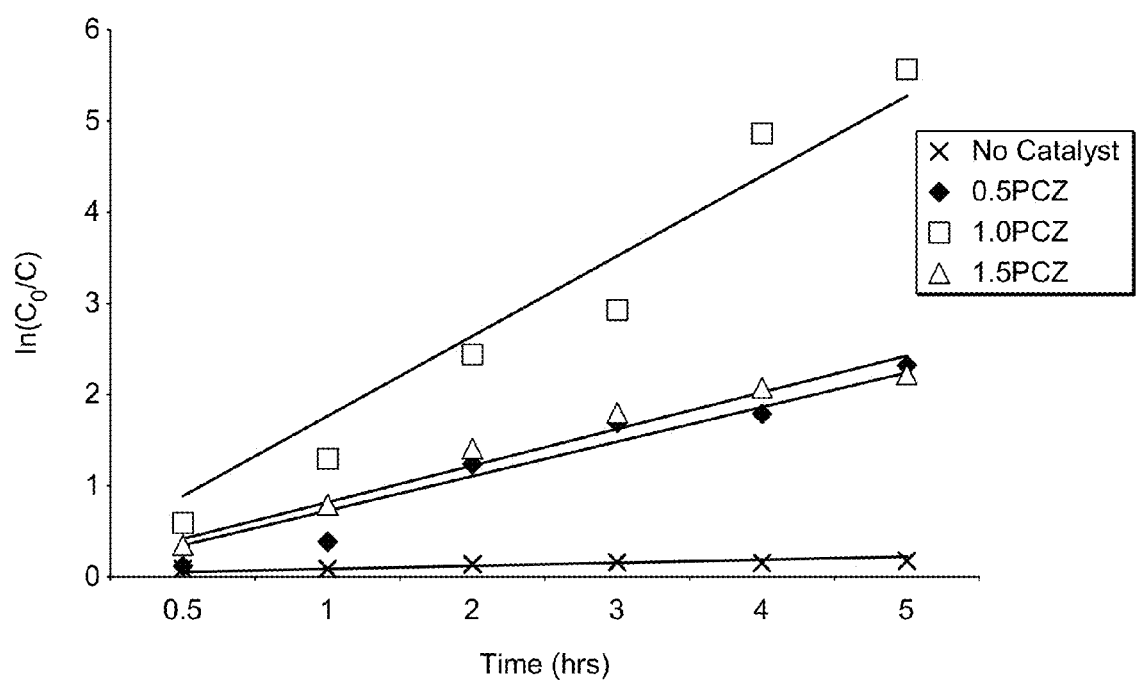
FIG. 9 shows reaction kinetics of photo-catalytic degradation of MTBE in water in presence of Pd doped $Ce_2O_3$—ZnO catalyst.

The rate constant of this reaction was observed from the slope of the plot FIG. 9 [Hayat et al. 2011]. It was found that the rate constant of the photo-degradation reaction increases with the percentage of the Pd and start to decrease after certain optimum doping level. FIG. 9 shows that 1% Pd/Ce$_2$O$_3$—ZnO photo-catalyst gives the highest rate constant (0.87 h$^{-1}$), while the rate constant obtained for 0.5% Pd/Ce$_2$O$_3$—ZnO photo-catalyst and 1.5% Pd/Ce$_2$O$_3$—ZnO photo-catalyst are 0.37 h$^{-1}$ and 0.4 h$^{-1}$, respectively. Thus, the kinetics of photo-catalytic degradation reaction of MTBE was observed as first order kinetics.

While the present disclosure has been described with reference to an exemplary embodiment, changes may be made within the purview of the appended claims, without departing from the scope and spirit of the present disclosure in its aspects. Also, although the present disclosure has been described herein with reference to particular materials and embodiments, the present disclosure is not intended to be limited to the particulars disclosed herein; rather, the present disclosure extends to all functionally equivalent structures, methods and uses, such as are within the scope of the instant claims. Accordingly, the specification and drawings are to be regarded in an illustrative rather than in a restrictive sense.

What is claimed is:

1. A method, comprising:
    dissolving a pre-determined amount of a palladium(II)(Pd) nitrate dihydrate (Pd(NO$_3$)$_2$.2H$_2$O) in a deionized water to form a solution, wherein the solution is enough to cover a cerium oxide-zinc oxide particle (Ce$_2$O$_3$—ZnO particle);
    mixing Ce$_2$O$_3$—ZnO particle with Pd(NO$_3$)$_2$.2H$_2$O solution to form a Pd nitrate impregnated Ce$_2$O$_3$—ZnO particle;
    drying the Pd nitrate impregnated Ce$_2$O$_3$—ZnO particle;
    exposing the Pd nitrate impregnated Ce$_2$O$_3$—ZnO particle to ammonia vapors;

mixing and drying the Pd nitrate impregnated $Ce_2O_3$—ZnO particle; and calcining the Pd nitrate impregnated $Ce_2O_3$—ZnO particle to obtain a Pd/$Ce_2O_3$—ZnO photo-catalyst, wherein the photocatalyst is used for photo-catalytic degradation of a Methyl tertiary butyl ether (MTBE) in water.

2. The method of claim 1, wherein the Pd nitrate impregnated $Ce_2O_3$—ZnO particle is dried at a heating rate of 0.33° C./min from room temperature to 85° C.

3. The method of claim 1, wherein calcination of the dried Pd nitrate impregnated $Ce_2O_3$—ZnO particle is carried at 450° C. for 6 hours to obtain a Pd/$Ce_2O_3$—ZnO photo-catalyst.

4. The method of claim 1, wherein the pre-determined amount of palladium(II) nitrate dihydrate ($Pd(NO_3)_2.2H_2O$) is in the range of 0.5% to 1.5%.

5. The method of claim 1, wherein the pre-determined amount of palladium(II) nitrate dihydrate ($Pd(NO_3)_2.2H_2O$) is 0.5 wt % of Pd.

6. The method of claim 1, wherein the pre-determined amount of palladium(II) nitrate dihydrate ($Pd(NO_3)_2.2H_2O$) is 1.0 wt % of Pd.

7. The method of claim 1, wherein the pre-determined amount of palladium(II) nitrate dihydrate ($Pd(NO_3)_2.2H_2O$) is 1.5 wt % of Pd.

8. The method of claim 1, wherein the photocatalyst result in 99.6% of MTBE degradation in water.

* * * * *